US006562758B1

(12) United States Patent
Evans et al.

(10) Patent No.: US 6,562,758 B1
(45) Date of Patent: May 13, 2003

(54) METHODS AND COMPOSITIONS TO DEFOLIATE CROP PLANTS AND MINIMIZE PLANT REGROWTH FOLLOWING DEFOLIATION

(75) Inventors: John R. Evans, Raleigh, NC (US); Richard R. Evans, Greenville, MS (US); Anita Harrell, Apex, NC (US); Wade W. Stewart, Brandon, MS (US); Dave King, Santa Clara, CA (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 09/461,383

(22) Filed: Dec. 15, 1999

(51) Int. Cl.$^7$ .......................... A01N 43/40; A01N 57/02
(52) U.S. Cl. ................... 504/128; 504/165; 504/167
(58) Field of Search ..................... 504/128, 165, 504/167

(56) References Cited

U.S. PATENT DOCUMENTS

| | | | |
|---|---|---|---|
| 3,879,188 A | 4/1975 | Fritz et al. | 71/86 |
| 4,240,819 A | 12/1980 | Fritz et al. | 71/76 |
| 4,352,869 A | 10/1982 | Mellors | 429/191 |
| 4,374,661 A | 2/1983 | Fritz et al. | 71/86 |
| 4,401,454 A | 8/1983 | Fritz et al. | 71/76 |
| 4,613,354 A | 9/1986 | Rusch | 71/73 |
| 4,840,660 A * | 6/1989 | Kowite et al. | 71/86 |
| 4,933,001 A | 6/1990 | Plath et al. | 71/96 |
| 4,960,275 A | 10/1990 | Magon | 71/73 |
| 5,098,462 A | 3/1992 | Anderson et al. | 71/88 |
| 5,098,466 A * | 3/1992 | Anderson et al. | 71/94 |
| 5,123,951 A | 6/1992 | See et al. | 71/86 |
| 5,123,955 A | 6/1992 | Plath et al. | 71/95 |
| 5,888,931 A | 3/1999 | Anderson et al. | 504/130 |

FOREIGN PATENT DOCUMENTS

| | | |
|---|---|---|
| DE | 3643657 A1 | 6/1998 |
| DE | 199 11 165 A1 | 9/2000 |

OTHER PUBLICATIONS

Gan et al. "Making Sense of Senescence". Plant Physiology. 113:313–319, 1997.*
Database CAB, Online!, XP002168008.
Electronic pesticide manual (Eleventh Edition) Version 1.1, 1999, XP002168003, Database Cropu, Online!, XP002168009.
Electronic pesticide manual (Eleventh Edition) Versio 1.1, 1999, XP002168004.
Electronic pesticide manual (Eleventh Edition) Versio 1.1, 1999, XP002168005.
Electronic pesticide manual (Eleventh Edition) Versio 1.1, 1999, XP002168006.
Electronic pesticide manual (Eleventh Edition) Versio 1.1, 1999, XP002168007.
Database Cropu, Online!, XP002168010.
Database Chemicabs, XP0021688011.

* cited by examiner

Primary Examiner—S. Mark Clardy
(74) Attorney, Agent, or Firm—Nixon & Vanderhye P.C.

(57) ABSTRACT

Concurrent or sequential application of an auxin transport inhibitor and a defoliating agent synergistically improve defoliation of crop plants and minimize crop plant regrowth. Preferably, the auxin transport inhibitor is a semicarbazone compound. The defoliating agent may be an ethylene response or ethylene-type response agent such as a phosphonic acid derivative. Most preferably, the semicarbazone compound is diflufenzopyr and the phosphonic acid derivative is ethephon (i.e., ethephon (2-chloroethyl) phosphonic acid).

10 Claims, No Drawings

METHODS AND COMPOSITIONS TO DEFOLIATE CROP PLANTS AND MINIMIZE PLANT REGROWTH FOLLOWING DEFOLIATION

FIELD OF THE INVENTION

The present invention relates to the defoliation of crop plants. In preferred forms, the present invention is embodied in compositions and processes whereby crop plants (e.g., cotton) may be defoliated prior to harvest and/or to compositions which effectively prevent regrowth of defoliated crop plants.

BACKGROUND AND SUMMARY OF THE INVENTION

Cotton is the most widely used textile fiber and is grown around the world. The cotton plant (*Gossypium hirsutum*) is a perennial plant of tropical origins that is cultivated in an annual manner in temperate regions.

The cotton plant continually produces fruit (bolls) starting at the seven to nine leaf stage through the end of the season. Generally, the bolls produced in the early part of the growing season obtain a larger size by harvest than the bolls produced in the last part of the growing season. The bolls produced in the first part of the season will open several days or weeks before the bolls produced in the last part of the season. However, once open, the cotton bolls begin to lose fiber quality due to the continued exposure to weather. For this reason, it benefits the cotton grower to begin harvesting before the plants are completely mature.

When cotton plants are mechanically harvested while green leaves remain on the plant, a green stain will often be visibly present on the cotton fiber during the harvesting process. This green stain reduces the value of the fiber at market. For this reason, a defoliation agent is often applied to the cotton plants before they are mechanically harvested. Although defoliation of cotton plants has been practiced in the past, there is still a need for improvement.

Broadly, the present invention relates to the discovery that the concurrent or sequential application of a plant growth regulator (preferably, an auxin transport inhibitor) and a defoliation agent (preferably, an ethylene response or ethylene-type response inducing agent) synergistically improve defoliation of crop plants and/or will minimize (if not prevent entirely) plant regrowth following defoliation. Preferably, the auxin transport inhibitor is a semicarbazone compound and the ethylene response or ethylene-type response agent is a phosphonic acid derivative. Most preferably, the semicarbazone compound is diflufenzopyr and the phosphonic acid derivative is ethephon (i.e., ethephon (2-chloroethyl) phosphonic acid).

Other aspects and advantages of the present invention will become more clear after careful consideration is given to the following detailed description of the preferred exemplary embodiments thereof.

DETAILED DESCRIPTION OF THE INVENTION

The preferred auxin transport inhibitors that may be employed in the practice of the present invention include substituted semicarbazones and related compounds, such as thiosemicarbazones and isothiosemicarbzones and salts thereof, as described more fully in U.S. Pat. Nos. 5,098,462 and 5,098,466 (the entire content of each U.S. patent being expressly incorporated hereinto by reference). These compounds may be synthesized by reacting a carbonyl compound and a semicarbazide or thiosemicarbazide together at room temperature in the presence of an alcohol solvent, such as methanol or ethanol and with or without an acid catalyst to give the semicarbazones that may be employed in the practice of the present invention. The most preferred semicarbazone employed in the practice of this invention is diflufenzopyr.

The preferred ethylene response or ethylene-type response inducing agent is a compound of the following formula:

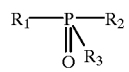

wherein:
$R_1$ is haloethyl, and $R_2$ and $R_3$ are selected from (1) a chlorine atom and a hydroxy group, (2) the group —$OR_4$ and the group —O—$CH_2R_4$ wherein each $R_4$ is one member of the group of unsubstituted aryl, substituted aryl and a heterocyclic group, (3) the group —$OR_4$ and the group —O—$CH_2R_4$ wherein each $R_4$ is a different member of the group of hydrogen, unsubstituted alkyl, substituted alkyl, unsubstituted cycloalkyl, substituted cycloalkyl, unsubstituted aryl, substituted aryl, a heterocyclic group, alkene and alkyne, provided that when one $R_4$ is selected from unsubstituted alkyl, substituted alkyl, alkene and alkyne, the other $R_4$ is selected from unsubstituted aryl, substituted aryl and a heterocyclic group, (4) together $R_2$ and $R_3$ represent the group:

where $R_5$ and $R_6$ are each connected to the phosphorous atom by a separate single bond, and where one of $R_5$ and $R_6$ is —O— and the other is selected from the group of —O—, —$OCH_2$, —CO—O— and —CONH, and $R_7$ represents a cyclic group selected from benzene, substituted benzene, a heterocyclic ring and a substituted heterocyclic ring, (5) one of $R_2$ and $R_3$ is —$OR_8$ and the other is:

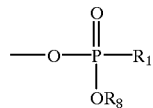

wherein each $R_8$ is the same or different and is selected from hydrogen, unsubstituted alkyl, substituted alkyl, unsubstituted aryl, substituted aryl and a heterocyclic group, and wherein $R_1$ is as defined above.

Suitable ethylene response and ethylene-type response inducing agents within the definition above are described in U.S. Pat. Nos. 3,879,188, 4,240,819, 4,352,869, 4,374,661, 4,401,454 and 5,123,951, the entire content of each such patent being incorporated expressly hereinto by reference. The most preferred ethylene inducing agent is 2-chloroethyl-phosphonic acid colloquially known as ethephon as well as its immediate derivatives.

Specific phosphonic acid derivative compounds usable in the practice of the present invention include the bis(acid chloride) or 2-chloroethylphosphonic acid, the pyrocatechol cyclic ester of 2-chloroethylphosphonic acid, the 4-chloropyrocatechol cyclic ester of 2-chloroethylphosphonic acid, the mixed ethyl and 2-hydroxyphenyl diester of 2-chloroethyl-phosphonic acid, the mixed butyl and 2-hydroxyphenyl diester of 2-chloroethyl-phosphonic acid, the 2-chloroethyl monoester of 2-chloroethylphosphnic acid, 2-bromoethylphosphonic acid, the bis(phenyl)ester of 2-chloroethylphosphonic acid, the tetrachloropyrocatechol cyclic ester of 2-chloroethylphosphonic acid, 2-iodoethylphosphoic acid, the saligen cyclic ester of 2-chloroethylphosphonic acid, salicyclic acid cyclic ester of 2-chloroethylphosphonic acid, the ethyl monoester of 2-bromoethylphosphonic acid, the butyl monoester of 2-iodoethylphosphonic acid, the 3-hydroxyphenyl monoester of 2-chloroethylphosphonic acid (which exists in polymeric form), the bis(2-oxoprrolidinylmethyl) ester of 2-chloroethylphosphonic acid, the o-hydroxyphenyl monoester of 2-chloroethylphosphonic acid, the mixed isopropyi and 2-hydroxyphenyl diester of 2-chloroethylphosphonic acid, 2-fluoroethylphosphonic acid, the mixed octyl and 2-hydroxyphenyl diester of 2-chloroethylphosphonic acid, the mixed hexadecyl and 2-hydroxyphenyl diester of 2-chloroethylphosphonic acid, the mixed tridecyl and 2-hydroxyphenyl diester of 2-chloroethylphosphonic acid, the anhydride of 2-chloroethylphosphonic acid, 2-chloroethylphosphonic acid, the mixed butyl and 2-hydroxyphenyl diester of 2-chloroethylphosphonic acid, and the 2-bromoethyl monoester of 2-bromoethylphosphonic acid.

Other useful phosphonic acid derivative compounds within the above formula include salicyclic acid cyclic ester of phosphonamidic acid, the mixed phenyl and 2-hydroxyphenyl diester of 2-chloroethylphosphonic acid, 2-chloroethyldichlorophosphine, the bis (pentachlorophenyl) ester of 2-chloroethylphosphonic acid; 2-chloropropylphosphonic acid, 2-phenylthioethylphosphonic acid, the 2,3-pyridinedio cyclic ester of 2-chloroethylphosphonic acid, 2-chloroethylthiophosphonic acid, (2-bromo, 2-fluoro and 2-iodo) and 2-chloroethyl-2,3-dibromo4-hydroxy-2-butenyl ester polymer. Salts of the phosphonic derivatives of this invention may be used. Examples of such salts include the sodium, aluminum, zinc, potassium and lithium salts.

The semicarbazone is applied to the locus of growing crop plants at rates ranging between 0.005 to about 0.09, and more preferably between about 0.01 to 0.05, pounds of active ingredient per acre (lb. ai/A). The ethylene response or ethylene-type response inducting agent, on the other hand, is most preferably applied to the locus of the plant in an amount between about 0.25 to about 2.5 lb. ai/A, more preferably in an amount between about 0.5 to about 2.0 lb ai/A. The active ingredients may be applied concurrently to the plant (e.g. as part of a tank mixture of ingredients), or may be applied sequentially. If applied sequentially, it is most preferred that the semicarbazone compound be applied to the locus of the growing plant first, followed within at least about 3 to about 21 days of the semicarbazone compound application, by the application of the ethylene response or ethylene-type response inducing agent. When applied sequentially, then the respective amounts of active ingredient applied should be within the ranges noted above.

The active ingredients may be applied either collectively or sequentially in the form of dusts, granules, solutions, emulsions, wettable powders, flowables and suspensions. Application of a compound as an active ingredient is made according to conventional procedure to the locus of the plant in need of the same using the appropriate amount of the compound per acre as will be described below. According to the present invention the application of the compound to the "locus" of the plant includes application to the plant or parts of the plant or the soil in which the plant is growing.

The active ingredients be applied to above ground portions of the plants. The application of liquid and particulate solid compounds and/or compositions to above ground portions of plants may be carried out by conventional methods, for example, boom and hand application, including sprayers or dusters. The compounds and/ or compositions may be applied aerially as a spray, if desired. The active ingredients employed in the practice of the present invention are most preferably used in the form of aqueous solutions. The solutions may be applied in a conventional manner, for example, by spraying, atomizing or watering the locus of the plant.

The active ingredients may also be applied in conjunction with other ingredients or adjuvants commonly employed in the art. Examples of such ingredients include drift control agents, defoaming agents, preservatives, surfactants, fertilizers, phytotoxicants, herbicides, pesticides, insecticides, fungicides, wetting agents, adherents, nematocides, bactericides, trace elements, synergists, antidotes, mixtures thereof and other such adjuvants well known in the plant growth regulating art.

The present invention will be further illustrated by way of the following non-limiting examples.

EXAMPLES

In the Examples which follow, PREP™ Brand ethephon (ETP) for cotton and tobacco commercially available from Rhône-Poulenc Ag company was employed which contained as active ingredient ethephon (2-chloroethyl) phosphonic acid in an amount of 55.4%.

Example 1

ETP and diflufenzopyr (DFP) were applied to greenhouse grown red kidney bean plants and cotton plants alone and as a mixture in combination with one another. The percent defoliation of the treated plants was determined three and fourteen days after treatment (DAT), with the percent regrowth also being determined fourteen days after treatment for the kidney bean plants, and both fourteen and twenty-eight days after treatment for the cotton plants. The results for the kidney bean plants are shown in Table 1A below, while the results for the cotton plants are shown in Table 1B below:

TABLE 1A

|  |  | % Defoliation | | % Regrowth |
| --- | --- | --- | --- | --- |
|  | lb. ai/A | 3 DAT | 14 DAT | 14 DAT |
| Untreated | 0 | 0 | 0 | 100 |
| ETP | 2.0 | 6 | 35 | 10 |
| DFP | 0.050 | 7 | 23 | 0 |
| DFP | 0.010 | 2 | 22 | 0 |
| DFP | 0.001 | 0 | 4 | 100 |
| ETP + DFP | 2.0 + .0050 | 88 | 100 | 0 |
| ETP + DFP | 2.0 + 0.010 | 94 | 100 | 0 |
| ETP + DFP | 2.0 + 0.001 | 47 | 59 | — |

TABLE 1B

|  | lb. ai/A | % Defoliation | | % Regrowth | |
| --- | --- | --- | --- | --- | --- |
|  |  | 3 DAT | 14 DAT | 14 DAT | 28 DAT |
| Untreated | 0 | 13 | 13 | 100 | 100 |
| ETP | 2.0 | 31 | 49 | 8 | 77 |
| DFP | 0.050 | 31 | 49 | 2 | 0 |
| DFP | 0.010 | 34 | 41 | 5 | 6 |
| DFP | 0.001 | 12 | 51 | 50 | 9 |
| ETP + DFP | 2.0 + .0050 | 71 | 83 | 0 | 0 |
| ETP + DFP | 2.0 + 0.010 | 53 | 67 | 2 | 8 |
| ETP + DFP | 2.0 + 0.001 | 44 | 76 | 8 | 30 |

The data in Tables 1A and 1B demonstrate that either ethephon or diflufenzopyr provide poor defoliation of 51% or less in greenhouse tests on kidney bean and cotton plants. Ethephon used alone tended to reduce plant height and drop a few leaves. Diflufenzopyr produced epinasty (twisting of new growth and/or cupping of leaves) at rates of 0.01 and 0.05 lb ai/A and reduced growth. The epinasty produced by diflufenzopyr was severe on kidney beans. The data demonstrate, however, that ethephon and diflufenzopyr at rates of 0.01 and 0.05 lbs ai/A provide defoliation greater than either product used alone in greenhouse tests. Regrowth from the combination of ethephon and high rates of diflufenzopyr was less than the regrowth that occurred from ethephon when used alone.

Example 2

Example 1 was repeated in a field study in Mississippi. The percent defoliation of the plants was examined and appears in Table 2 below.

TABLE 2

|  | lb. ai/A | % Defoliation | |
| --- | --- | --- | --- |
|  |  | 7 DAT | 20 DAT |
| Untreated | — | 0 | 0 |
| DFP | .005 | 23 | 40 |
| DFP | .010 | 23 | 39 |
| DFP | .020 | 21 | 39 |
| DFP + ETP | .005 + 1.0 | 64 | 70 |
| DFP + ETP | .010 + 1.0 | 76 | 80 |
| DFP + ETP | .020 + 1.0 | 71 | 70 |
| ETP | 1.0 | 58 | 78 |
| ETP+ (Note 1) | 2.25 | 86 | 93 |
| Def ® 6 | 1.9 | 85 | 88 |

Notes:
(1) ETP+ is FINISH ® Brand harvest aid for cotton containing 35.1% ethephon, and 4.3% cyanilide (1-(2,4-dichlorophenylaminocarbonyl)-cyclopropane carboxylic acid) available commercially from Rhone-Poulenc Ag Company
(2) Def ® 6 is an emulsifiable defoliant commercially available from Bayer Corporation which contains S,S,S-tributyl phosphorotrithioate as an active ingredient.

The data above show an improvement in defoliation with the combination of ethephon and diflufenzopyr at rates of 0.005 to 0.020 lbs ai/A as compared to either product alone, especially at seven days after treatment.

Example 3

Greenhouse grown red kidney bean plants were treated with either a tank mixed, or sequential applications of DFP and ETP. In this example, DFP was applied at a rate of 0.005 lb. ai/A. For the sequential application, DFP was applied at intervals 3, 14 and 21 days prior to the application of ETP. ETP was applied in an amount of 0.1 lb ai/A and 0.4 lb ai/A. The results appear in Table 3 below.

TABLE 3

| Treatment(s) | Application Technique | Application Date (Days) | % Defoliation | |
| --- | --- | --- | --- | --- |
|  |  |  | 0.1 lb/A ETP | 0.4 lb/A ETP |
| ETP | na | 0 | 18 | 20 |
| DFP | Tank Mixed | 0 | 74 | 100 |
| ETP |  | 0 |  |  |
| DFP | Sequential | 0 | 68 | 76 |
| ETP | Application | 3 |  |  |
| DFP | Sequential | 0 | 33 | 79 |
| ETP | Application | 14 |  |  |
| DFP | Sequential | 0 | 56 | 83 |
| ETP | Application | 21 |  |  |

Notes:
(1) All treatments had Dash ® HC spray adjuvant at 1% v/v.
The data in Table 3 above demonstrate that pretreatment of kidney beans in the greenhouse with diflufenzopyr at 3, 14 and 21 days before the application of ethephon enhanced defoliation as compared to ethephon alone.

Example 4

Example 3 was repeated with greenhouse grown kidney beans with the results being set forth in Table 4 below.

TABLE 4

| Treatment(s) | Rates lbs ai/A | Application Dates | % Defoliation 15 DAT |
| --- | --- | --- | --- |
| Untreated | — | — | 0 |
| ETP | 1.0 | 7 | 28 |
| DFP | 0.005 | 7 | 58 |
| ETP | 1.0 | 7 |  |
| DFP | 0.005 | 0 | 59 |
| DFP | 0.005 | 0 | 73 |
| ETP | 1.0 | 7 |  |

The data above show that pretreatment of kidney beans with DFP seven days before the application of ETP increased the defoliation activity of the later compound.

Example 5

Field grown potato plants were treated with mixtures of DFP and ETP in the amounts set forth below in Table 5. Potatoes are typically defoliated with a material such as paraquat prior to digging. The percent of defoliation of the potato plants was examined 4 and 18 days after treatment, with the data appearing in Table 5 below.

TABLE 5

| Treatment(s) | Rates lbs ai/A | Percent Defoliation | |
| --- | --- | --- | --- |
|  |  | 4 DAT | 15 DAT |
| Untreated | — | 0 | 29 |
| DFP + ETP | 0.02 + 1.0 | 39 | 63 |
| DFP + ETP | 0.04 + 1.0 | 45 | 79 |
| DFP + ETP | 0.06 + 1.0 | 45 | 85 |
| DFP + ETP | 0.02 + 0.5 | 34 | 66 |
| DFP + ETP | 0.04 + 0.5 | 39 | 66 |
| DFP + ETP | 0.06 + 0.5 | 36 | 60 |
| Paraquat | 0.45 | 76 | 44 |

Notes:
(1) All DFP + ETP treatments had Dash ® HC spray adjuvant at 1% v/v.

Example 6

Example 2 was repeated using field grown cotton plants in Louisiana (LA), Georgia (GA) and North Carolina (NC) using between 0.03 to 0.09 lbs ai/A of DFP with and without ETP. The percent regrowth of the plants was examined at selected days after treatment (DAT) at each facility, with the data appearing in Table 6 below.

TABLE 6

|  | Rate (lb. ai/A) | % Regrowth LA 17 DAT | GA 15 DAT | NC 27 DAT | Avg. |
|---|---|---|---|---|---|
| Untreated | — | 76.3 | 40.3 | 60.0 | 59 |
| DFP | 0.030 | 2.5 | 18.0 | 1.7 | 7 |
| DFP | 0.060 | 1.8 | 13.0 | 5.0 | 7 |
| DFP | 0.090 | 0.5 | 17.8 | 0.0 | 6 |
| DFP + ETP | 0.030 + 1.0 | 50.0 | 34.0 | 6.7 | 30 |
| DFP + ETP | 0.060 + 1.0 | 36.3 | 33.8 | 0.0 | 23 |
| DFP + ETP | 0.090 + 1.0 | 12.5 | 10.0 | 3.3 | 9 |
| ETP | 1.0 | 83.8 | 8.5 | 60.0 | 51 |
| ETP+ | 1.68 | 87.5 | 24.8 | 58.3 | 57 |
| Def ® 6 | 1.9 | 92.5 | 36.5 | 30.0 | 43 |

The data above demonstrate that, surprisingly, adding DFP to ETP reduced the amount of regrowth.

Example 7

Example 6 was repeated using field grown cotton plants in Mississippi (MS). The percent regrowth following defoliation was determined 20 days after treatment (20 DAT) with the data appearing in Table 5 below.

TABLE 7

| Treatment(s) | Rates lbs ai/A | % Regrowth 20 DAT |
|---|---|---|
| Untreated | — | — |
| DFP | 0.005 | 31.3 |
| DFP | 0.010 | 15.0 |
| DFP | 0.20 | 11.3 |
| DFP + ETP | 0.005 + 1.0 | 21.3 |
| DFP + ETP | 0.010 + 1.0 | 10.0 |
| DFP + ETP | 0.020 + 1.0 | 8.8 |
| ETP | 1.0 | 36.3 |
| ETP+ | 2.25 | 20.0 |
| Def ® 6 | 1.9 | 16.3 |

Example 8

Greenhouse studies on kidney beans were conducted using combinations of DFP and other defoliation or desiccation agents as follows:

BASF 123W: cinidon-ethyl (See, U.S. Pat. Nos. 4,933,001 and 5,123,955, the entire content of each being expressly incorporated hereinto by reference).

DEF® 6: See Note 1 of Example 2.

DROPP® 50WP: thidiazuron cotton defoliant commercially available from AgroEvo.

In these greenhouse studies, leaves were clipped off the kidney beans at seven (7) days after treatment (DAT) on four of the six replications to encourage uniform regrowth. The data appear in Tables 8A–8C below, wherein the percent regrowth was determined as a percent of the untreated check plants.

TABLE 8A

| BAS 123W (lbs ai/A) | DFP (lbs ai/A) 0 | 0.001 | 0.002 | 0.004 |
|---|---|---|---|---|
|  | % Regrowth at 21 DAT | | | |
| 0 | 100 | 12 | 4 | 3 |
| 0.03 | 124 | 17 | 1 | 0.0 |
| 0.06 | 110 | 12 | 3 | 0.0 |
| 0.12 | 73 | 4 | 6 | 0.0 |

TABLE 8B

| DEF ® 6 (lbs ai/A) | DFP (lbs ai/A) 0 | 0.001 | 0.002 | 0.004 |
|---|---|---|---|---|
|  | % Regrowth at 21 DAT | | | |
| 0 | 100 | 60 | 20 | 0.0 |
| 0.375 | 190 | 55 | 8 | 0.0 |
| 0.75 | 252 | 57 | 5 | 0.0 |
| 0.12 | 200 | 75 | 0.0 | 0.0 |

TABLE 8C

| DROPP ® 50 WP (lbs ai/A) | DFP (lbs ai/A) 0 | 0.001 | 0.002 | 0.004 |
|---|---|---|---|---|
|  | % Regrowth at 21 DAT | | | |
| 0 | 100 | 47 | 20 | 18 |
| 0.05 | 95 | 102 | 90 | 53 |
| 0.1 | 74 | 95 | 88 | 54 |
| 0.2 | 87 | 78 | 77 | 63 |

As can be seen from the above data, the use of DFP by itself reduced regrowth as compared to the untreated check. The use of BASF 123W and DEF® 6 tended to promote regrowth. Combining BAS 123W or DEF® 6 with DFP at 0.004 lbs ai/A significantly reduced regrowth. The use of DROPP® 50WP slightly suppressed regrowth. Combining DROPP® 50WP with DFP at 0.004 lbs ai/A significantly reduced regrowth as compared to the use of DROPP® 50WP alone.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of defoliating crop plants and minimizing regrowth following defoliation comprising applying to the locus of a growing crop plant in need of defoliation a defoliating effective amount of between about 0.005 to about 0.09 lb ai/A of diflufenzopyr and between about 0.25 to about 2.5 lb ai/A of ethephon.

2. The method of claim 1, wherein the diflufenzopyr and ethephon are applied concurrently to the locus of the plant.

3. The method of claim 2, wherein the diflufenzopyr and ethephon are applied to the locus of the plant in the form of a mixture.

4. The method of claim 1, wherein the diflufenzopyr is first applied to the locus of the plant followed by the application of the ethephon.

5. The method of claim 4, wherein the ethephon is applied to the locus of the plant within about three days or more following application of the diflufenzopyr to the locus of the plant.

6. The method of claim 5, wherein the ethephon is applied to the locus of the plant within about three to about 21 days following application of the diflufenzopyr to the locus of the plant.

7. The method of claims 1–6, wherein the diflufenzopyr is applied to the locus of the plant in an amount between about 0.01 to about 0.05 lb. ai/A, and wherein the ethephon is applied to the locus of the plant in an amount between about 0.5 to about 2.0 lb. ai/A.

8. The method of claim 1, wherein the plant is selected from the group consisting of cotton, red kidney bean and potato plants.

9. A plant composition of defoliating crop plants and minimizing plant regrowth, which composition comprises a plant defoliating regrowth minimizing effective amount of between about 0.005 to about 0.09 lb ai/A of diflufenzopyr and between about 0.25 to about 2.5 lb ai/A of ethephon.

10. The composition of claim 9, wherein the diflufenzopyr is present an amount between about 0.01 to about 0.05 lb. ai/A, and wherein the ethephon is present in an amount between about 0.5 to about 2.0 lb. ai/A.

* * * * *